United States Patent [19]

Desobry

[11] Patent Number: 5,075,467
[45] Date of Patent: Dec. 24, 1991

[54] PROCESS FOR THE PREPARATION OF TITANOCENES CONTAINING O,O'-DIFLUOROARYL LIGANDS

[75] Inventor: Vincent Desobry, Marly, Switzerland

[73] Assignee: Ciba-Geigy Corporation, Ardsley, N.Y.

[21] Appl. No.: 527,990

[22] Filed: May 23, 1990

[30] Foreign Application Priority Data

Jun. 1, 1989 [CH] Switzerland .................. 2053/89

[51] Int. Cl.$^5$ ............................................. C07F 17/00
[52] U.S. Cl. .................................. 556/53; 556/56; 430/281
[58] Field of Search ............. 430/947, 925, 281; 556/51, 53, 56

[56] References Cited

U.S. PATENT DOCUMENTS 4,590,287  5/1986  Riediker et al. ............... 556/53
4,910,121  3/1990  Riediker et al. ............... 430/281
4,970,136  9/1990  Riediker et al. ............... 430/286

FOREIGN PATENT DOCUMENTS 0122223  9/1985  European Pat. Off. .
0255486  2/1988  European Pat. Off. .
0256981  2/1988  European Pat. Off. .
0318893  6/1989  European Pat. Off. .
0318894  6/1989  European Pat. Off. .

OTHER PUBLICATIONS

Journal of Organic Chemistry, 46, pp. 313–321 (1972).
Journal of Organic Chemistry, 74, pp. 85–90 (1974).
Müller, *Methoden Der Organischen Chemie*, 98–99 (1970).
Derwent Abst. 88-030671/05.
Derwent Abst. 88-051708/08.
Derwent Abst. 89-166941/23.
Derwent Abst. 89-166942/23.
J. Chem. Soc. 1962, 3227–3231.
J. Organomet. Chem. 1965, 446–454.
Methoden der Organischen Chemie, Houben-Weyl, vol. XIII/1, 1970 (Georg Thieme Verlag, Stuttgart).

*Primary Examiner*—John Niebling
*Assistant Examiner*—Steven P. Marquis
*Attorney, Agent, or Firm*—Harry Falber

[57] ABSTRACT

An improved preparation of titanocenes of the formula I

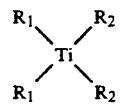

in which $R_1$ is cyclopentadienyl$^\ominus$, indenyl$^\ominus$ or 4,5,6,7-tetrahydroindenyl$^\ominus$, each of which is unsubstituted or monosubstituted or polysubstituted by $C_1$–$C_{18}$alkyl, $C_1$–$C_{18}$alkoxy, $C_2$–$C_{18}$alkenyl, $C_5$–$C_8$cycloalkyl, $C_6$–$C_{10}$aryl, $C_7$–$C_{16}$aralkyl, —Si(R$_3$)$_4$, —Ge(R$_3$)$_4$ or halogen, or the two $R_1$ radicals together are a divalent radical of the formula II

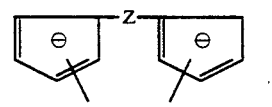

in which Z is —(CH$_2$)$_m$— where m = 1, 2 or 3, unsubstituted or phenyl-substituted $C_2$–$C_{12}$alkylidene, —Si(R$_3$.)$_2$— or —Si(R$_3$)$_2$—O—Si(R$_3$)$_2$—, and R$_3$ is $C_1$–$C_{12}$alkyl or $C_6$–$C_{10}$aryl, and $R_2$ is six-membered carbocyclic aromatic ring which is substituted by fluorine in both the ortho-positions to the Ti-C bond and which may also have further substituents, involves the addition of certain lithium amides .to a mixture of (R$_1$)$_2$TiX$_2$(X=halogen) and HR$_2$ at −30° C. to +25° C.

17 Claims, No Drawings

PROCESS FOR THE PREPARATION OF TITANOCENES CONTAINING O,O'-DIFLUOROARYL LIGANDS

The invention relates to an improved process for the preparation of titanocenes containing o,o'-difluoroaryl ligands, and novel titanocenes which can be prepared by this process.

It is known to prepare titanocenes containing polyfluorinated aryl ligands from the corresponding fluorinated aryllithium compounds and a titanocene dihalide. The aryllithium compound can—without being isolated—be prepared from the corresponding polyfluorobenzene and butyllithium, a hydrogen atom adjacent to two fluorine atoms being replaced by lithium. Tamborski et al., J. Organomet. Chem. 4 (1965), 446-454 have demonstrated this reaction sequence in the preparation of bis(cyclopentadienyl)bis(pentafluorophenyl)titanium:

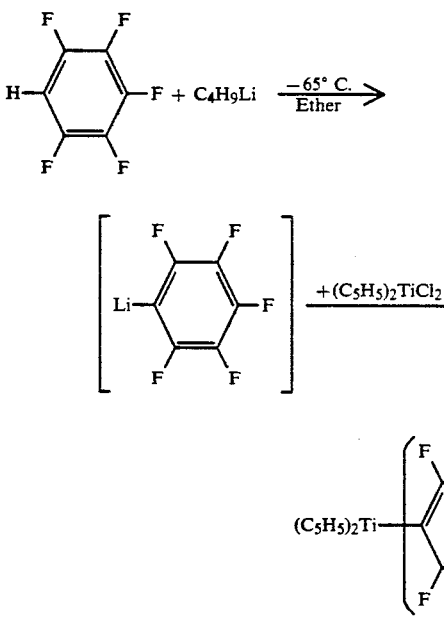

The pentafluorophenyllithium must be formed at very low temperatures since this compound is unstable at room temperature and decomposes rapidly even at $-10°$ C., as already shown by Coe et al., J. Chem. Soc. 1962, 3227.

For industrial use, a reaction at such low temperatures means a high energy requirement for cooling the reaction medium. However, it has now been found that the reaction or reaction sequence can be carried out at significantly higher temperatures if the metallation of the polyfluoroarene is carried out using a lithium amide and in the presence of the co-reactant titanocene dihalide. This is surprising, since amidation of the titanocene would be expected under these conditions. The reaction proved to be useful for a large number of fluoroarenes as long as they contain at least two fluorine atoms in the 1- and 3-positions. The metallation then takes place in the 2-position. The remaining positions of the arene may be occupied by hydrogen, alkyl or fluorine or by functional groups which do not react with the lithium amide or the lithiumarene.

The invention therefore relates to a process for the preparation of titanocenes of the formula I

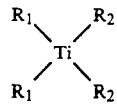

in which $R_1$ is cyclopentadienyl$^\ominus$, indenyl$^\ominus$ or 4,5,6,7-tetrahydroindenyl$^\ominus$, each of which is unsubstituted or monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{10}$aryl, $C_7$-$C_{16}$aralkyl, —Si($R_3$)$_3$, —Ge($R_3$)$_3$ or halogen, or both $R_1$ radicals together are a divalent radical of the formula II

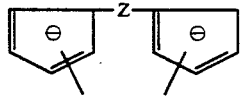

in which Z is —(CH$_2$)$_m$— where m=1, 2 or 3, unsubstituted or phenyl-substituted $C_2$-$C_{12}$alkylidene, —Si($R_3$)$_2$— or —Si($R_3$)$_2$—O—Si($R_3$)$_2$—, and $R_3$ is $C_1$-$C_{12}$alkyl or $C_6$-$C_{10}$aryl, $R_2$ is a six-membered carbocylic aromatic ring which is substituted by fluorine in both the ortho positions to the Ti-C bond and which, in addition, may be substituted by further fluorine atoms, by $C_1$-$C_4$alkyl or by one of the groups III to VII,

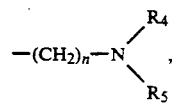

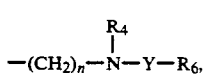

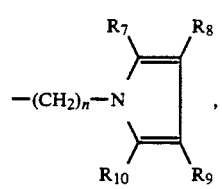

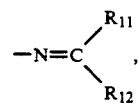

in which n is an integer from 0 to 6, $R_4$ is $C_1$-$C_{20}$alkyl, $C_3$-$C_{10}$cycloalkyl, $C_4$-$C_{20}$cycloalkylalkyl, $C_4$-$C_{20}$alkylcycloalkyl, $C_5$-$C_{20}$alkylcycloalkylalkyl, $C_6$-$C_{14}$aryl, $C_7$-$C_{20}$aralkyl, $C_7$-$C_{20}$alkaryl, $C_8$-$C_{20}$alkaralkyl, $C_3$-$C_{12}$alkoxyalkyl, tetrahydrofurfuryl or a —(CH$_2$CH$_2$O)$_p$—$C_1$-$C_{12}$alkyl radical where p=1-20, $R_5$ has one of the meanings given for $R_4$, or $R_4$ and $R_5$ together are $C_3$-$C_8$alkylene, which may be interrupted by —O—, —S— or —N($R_{14}$)—, or $R_4$ and $R_5$ together are —Si($R_3$)$_2$—CH$_2$CH$_2$—Si($R_3$)$_2$—, Y is —CO—, —CS—, —COO—, —CON($R_{14}$)—, —SO$_2$—, —SO$_2$N($R_{14}$)— or —Si($R_3$)$_2$—, $R_6$ is $C_4$-$C_{20}$alkyl, $C_2$-$C_{20}$alkaryl, $C_4$-$C_{10}$cycloalkyl, $C_5$-$C_{20}$cycloalkylalkyl, $C_5$-$C_{20}$alkylcycloalkyl, $C_6$-$C_{20}$alkylcycloalkylalkyl, $C_6$-$C_{14}$aryl, $C_7$-$C_{20}$aralkyl, $C_7$-$C_{20}$alkaryl or $C_8$-$C_{20}$alkarylalkyl, it being possible for these radicals to be unsubstituted or substituted by $C_1$-$C_{18}$alkoxy, $C_1$-$C_{18}$alkylthio or halogen, or $R_6$ and $R_4$ together are $C_4$-$C_8$alkylene, which may be interrupted by —O—, —S— or —N($R_{14}$)—, with the proviso that the C atom of $R_6$ which is adjacent to Y does not carry an H atom if Y is —CO—, —CS— or —SO$_2$—, $R_7$, $R_8$, $R_9$ and $R_{10}$, independently of one another, are hydrogen, $C_1$-$C_{18}$alkyl, $C_2$-$C_5$alkenyl, $C_7$-$C_9$phenylalkyl or $C_7$-$C_{12}$alkylphenyl, each of which is unsubstituted or substituted by $C_2$-$C_8$dialkylamino, bis[2-($C_1$-$C_4$alkoxy)ethyl]amino, morpholino, piperidino, $C_2$-$C_{12}$alkoxy, —(OCH$_2$CH$_2$)$_p$—O—$C_1$-$C_1$$_2$alkyl where p=1-20, 1,3-dioxolan-2-yl, $C_1$-$C_{12}$alkylthio or halogen, or are 2-furyl or —Si($R_3$)$_3$, $R_{11}$ is $C_1$-$C_{12}$alkyl which is unsubstituted or substituted by halogen, $C_1$-$C_{12}$alkoxy or $C_2$-$C_8$dialkylamino, or $C_6$-$C_{14}$aryl, $C_7$-$C_{20}$aralkyl $C_7$-$C_{20}$alkaryl or $C_8$-$C_{20}$alkarylalkyl, each of which is unsubstituted or substituted by $C_1$-$C_8$alkoxy, —(OCH$_2$CH$_2$)$_p$—O—$C_1$-$C_{12}$alkyl where p=1-20, $C_1$-$C_8$alkylthio, $C_2$-$C_8$dialkylamino, halogen or nitro, $R_{12}$ is hydrogen or has one of the meanings given for $R_{11}$, $R_{13}$ is $C_1$-$C_{18}$alkyl, $C_3$-$C_{12}$cycloalkyl, $C_2$-$C_5$alkenyl, glycidyl, —(CH$_2$CH$_2$O)$_p$—C$_1$-$C_{12}$alkyl where p=1-20, $C_6$-$C_{10}$aryl, $C_7$-$C_{20}$aralkyl, $C_7$-$C_{20}$alkaryl or $C_8$-$C_{20}$alkarylalkyl, it being possible for the aryl radicals to be substituted by $C_1$-$C_4$alkoxy, $C_1$-$C_4$alkylthio, $C_2$-$C_8$dialkylamino, halogen or nitro, or $R_{13}$ is $C_1$-$C_{20}$haloalkyl, —Si($R_3$)$_3$, —Sn($R_3$)$_3$ or 2-tetrahydropyranyl, and $R_{14}$ is $C_1$-$C_{12}$alkyl, $C_3$-$C_5$alkaryl or $C_7$-$C_9$phenylalkyl, by reacting a compound of the formula VIII

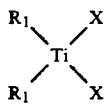    VIII in which X is Cl, Br or I, with LiR$_2$, which comprises reacting a mixture of 1 mole-equivalent of the compound of the formula VIII and 2 mole-equivalents of a compound HR$_2$ with 2 to 2.5 mole-equivalents of a lithium amide at −30° C. to +25° C. in an inert solvent, the lithium amide being a compound of the formula LiN($R_{15}$)($R_{16}$), in which $R_{15}$ and $R_{16}$, independently of one another, are 1-branched alkyl, cyclohexyl or phenyl, or $R_{15}$ and $R_{16}$, together with the N atom, are a 2,5-dialkylated pyrrolidine or a 2,6-dialkylated or 2,2,6,6-tetraalkylated piperidine.

The reaction is preferably carried out at −20° C. to +25° C., in particular at −15° C. to 0° C. 2.0 to 2.2 mole-equivalents of the lithium amide are preferably used per mole-equivalent of the compound of the formula VIII.

As in all reactions with organolithium compounds, the solvents used must be dry, and the use of a protective gas, for example nitrogen or argon, is advisable. In order to accelerate the reaction and to increase the yield, the reaction is preferably carried out in the presence of a polar solvent, in particular in mixtures of polar and non-polar solvents. Non-polar solvents which can be used are, in particular, hydrocarbons, such as alkanes, cyclohexane, benzene or toluene. Polar solvents which can be used are, in particular, ethers, for example diethyl ether or diisopropyl ether, tert-butyl methyl ether, anisole, ethylene glycol dialkyl ethers, diethylene glycol dialkyl ethers, tetrahydrofuran or dioxane, but also fully alkylated amides, for example tetramethylurea, hexamethylphosphoric triamide or N,N'-dimethyl-2-imidazolidinone. Mixtures of toluene and tetrahydrofuran or hexane and tetrahydrofuran in the approximate volume ratio 1:1 are particularly suitable.

The lithium amides LiN($R_{15}$)($R_{16}$) can be prepared, for example, by reacting the corresponding secondary amine HN($R_{15}$)($R_{16}$) with butyllithium or with lithium metal in the presence of naphthalene or styrene, see V. Schöllkopf in Methoden der Organischen Chemie [Methods of Organic Chemistry], volume XIII/1, page 98, G. Thieme-Verlag 1970. Individual lithium amides, for example lithium diisopropylamide, are commercially available. The lithium amides may alternatively be prepared in situ in the reaction mixture of the process according to the invention from the abovementioned components, advantageously before addition of or to the educt(s) I and VIII. In this respect, see also Example 1. The lithium amide preferably used is lithium diisopropylamide, lithium cyclohexylisopropylamide, lithium dicyclohexylamide and lithium 2,2,6,6-tetramethylpiperidide, in particular lithium diisopropylamide.

The compound of the formula VIII preferably used is one in which X is chlorine. A compound of the formula VIII in which $R_1$ is cyclopentadienyl$^\ominus$ or $C_1$-$C_4$alkyl-substituted cyclopentadienyl$^\ominus$, in particular cyclopentadienyl$^\ominus$ methylcyclopentadienyl$^\ominus$, is preferably used. Examples of compounds of the formula VIII are dicyclopentadienyltitanium dichloride and di(methylcyclopentadienyl)titanium dichloride.

The compound HR$_2$ preferably used is one in which R$_2$ is a monovalent radical of the formula IX

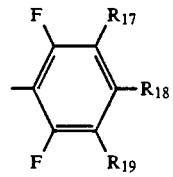    IX in which $R_{17}$, $R_{18}$ and $R_{19}$, independently of one another, are hydrogen, fluorine, $C_1$-$C_4$alkyl or a group of the formula III to VII.

These include compounds HR$_2$ in which R$_2$ is a radical of the formula IX in which $R_{17}$, $R_{18}$ and $R_{19}$, independently of one another, are H, F or CH$_3$. Examples of these are 1,3-difluorobenzene, 1,3,4-trifluorobenzene, 1,2,4,5-tetrafluorobenzene, pentafluorobenzene or 2,4-difluorotoluene.

Another group of compounds HR$_2$ comprises compounds in which R$_2$ is a radical of the formula IX in which $R_{17}$ or $R_{18}$ is a group of the formula III to VII, and the other radicals $R_{17}$, $R_{18}$ and $R_{19}$ are H or F. Of these compounds HR$_2$, those are preferred in which $R_{17}$ or $R_{18}$ is a group of the formula III to VII in which n is 0 or 1, in particular 0, $R_4$ is $C_1$-$C_{12}$alkyl, $C_3$-$C_{12}$alkoxy, phenyl, $C_7$-$C_9$phenylalkyl, cycloalkyl, cyclohexylmethyl or a —(CH$_2$CH$_2$O)$_p$—$C_1$-$C_4$alkyl group where p=1-5, $R_5$ has one of the meanings given for $R_4$, or $R_4$ and $R_5$ together are $C_4$-$C_5$alkylene, which may be interrupted by —O— or —N($R_{14}$)—, where $R_{14}$ is $C_1$-$C_4$alkyl, Y is —CO—, —SO$_2$— or —COO—, $R_6$ is $C_4$-$C_{12}$alkyl, phenyl or CH$_3$—, CH$_3$O— or Cl—substituted phenyl or $C_1$-$C_8$haloalkyl, or $R_6$ and $R_4$ together are $C_4$-$C_8$alkylene, with the proviso that the C atom of $R_6$ which is adjacent to Y does not carry a H atom, $R_7$, $R_8$, $R_9$ and $R_{10}$, independently of one another, are hydrogen, $C_1$-$C_8$alkyl, $C_2$-$C_{12}$alkoxyalkyl, $C_2$-$C_4$alkenyl, phenyl or 2-furyl, $R_{11}$ is phenyl which is unsubstituted or substituted by $C_1$-$C_{12}$alkyl, $C_1$-$C_4$alkoxy, $C_1$-$C_4$alkylthio, halogen or nitro, $R_{12}$ is hydrogen, and $R_{13}$ is $C_1$-$C_{14}$alkyl, —$(CH_2CH_2O)_p$—$C_1$-$C_{12}$alkyl where p=1-20, phenyl, benzyl, 2tetrahydropyranyl or —$Si(CH_3)_3$.

Compounds $HR_2$ which are preferably used are those in which $R_2$ is a radical of the formula IX in which either $R_{17}$ is a group of the formula III-VII and $R_{18}$ and $R_{19}$ are hydrogen, or in which $R_{18}$ is a group of the formula III-VII and $R_{17}$ and $R_{19}$ are fluorine.

Examples of such compounds $HR_2$ are:
1,2,4,5-tetrafluoro-3-(dimethylamino)benzene
1,2,4,5-tetrafluoro-3-morpholinobenzene
1,2,4,5-tetrafluoro-3-decyloxybenzene
1,3-difluoro-4-(dimethylaminomethyl)benzene
1,3-difluoro-4-decyloxybemzene
1,3-difluoro-4-ethoxybenzene
1,3-difluoro-4-(2-ethoxy)ethoxybenzene
N-(2,4-difluorophenyl)-N-hexyl-$\alpha$,$\alpha$-dimethylbutyramide
N-(2,4-difluorophenyl)-N-isopropylbenzamide
N-(2,4-difluorophenyl)-N-(3-phenylpropyl)pivalamide
N-(2,4-difluorophenyl)-N-hexylpivalamide
N-(2,4-difluorophenyl)-N-hexyl-$\alpha$,$\alpha$-dimethylvaleramide
N-(2,4-difluorophenyl)-N-butyl-$\alpha$,$\alpha$-dimethylvaleramide
N-(2,4-difluorophenyl)-N-ethylpropionamide
N-(2,4-difluorophenyl)-N-ethylisobutyramide
N-(2,4-difluorophenyl)-N-cyclohexylbenzamide
N-(2,4-difluorophenyl)-N-butyl-p-toluenesulfonamide
N-(2,4-difluorophenyl)-3,3-dimethylazetidin-2-one
N-(2,4-difluorophenyl)pyrrole
N-(2,4-difluorobenzyl)pyrrole
1-(2,4-difluorophenyl)-2,5-dimethylpyrrole
1-(2,4-difluorophenyl)-2,2,5,5-tetramethyl-1,2,5-azadisilolidine
1-[(2,4-difluorophenyl)methyl]-2,2,5,5-tetramethyl-1,2,5-azadisilolidine
N-(2,3,5,6-tetrafluorophenyl)pyrrole
N-(2,3,5,6-tetrafluorobenzyl)pyrrole
N-(2,3,5,6-tetrafluorophenyl)-N-hexyl-$\alpha$,$\alpha$-dimethylvaleramide
N-(3,5-difluorophenyl)pyrrole
N-benzal-2,4-difluoroaniline
N-(4-methylbenzal)-2,4-difluoroaniline
N-(4-methoxybenzal)-2,4-difluoroaniline
1,3-difluoro-4-butoxybenzene
1,3-difluoro-4-(trimethylsiloxy)benzene
1,3-difluoro-4-(2-tetrahydropyranyl)benzene
1,2,4,5-tetrafluoro-3-ethoxybenzene
1,2,4,5-tetrafluoro-3-dodecyloxybenzene
1,2,4,5-tetrafluoro-3-[2-(2-butoxy) -ethoxy]ethoxybenzene
1-(2,3,5,6-tetrafluorophenyl)-2,5-dimethylpyrrole The preparation of the azomethine educts is known to those skilled in the art and described in numerous textbooks of organic chemistry. Thus, the azomethine educts of the present invention can be prepared, for example, by reacting the appropriate primary amines with aldehydes.

In order to carry out the process it is advantageous to add a solution of hte lithium amide dropwise to a suspension or solution of the compound of the formula VIII and of the compound $HR_2$ with cooling and with stirring. The reaction proceeds rapidly and can be followed by analytical determination of the lithium amide or of the educts. In order to separate the lithium halide LiX formed, the reaction mixture can be poured into water and extracted with an organic solvent, or the reaction mixture is partially or fully evaporated, and the residue is extracted with an organic solvent in which LiX is insoluble, for example with dichloromethane. The crude product obtained by evaporating the organic solvent can be purified by crystallization or chromatography.

The products of the formula I are orange-red compounds which are stable at room temperature with exclusion of short-wave light. They can be used as photoinitiators for the photopolymerization of ethylenically unsaturated compounds. Some of these titanocenes of the formula I are known compounds and are described, for example, in EP-A-122,223, 255,486 and 256,981. Some of the products are novel compounds.

Novel compounds, and therefore further subject-matter of the invention, are compounds of the formula I

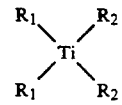

in which $R_1$ is cyclopentadienyl$^\ominus$, indenyl$^\ominus$ or 4,5,6,7-tetrahydroindenyl$^\ominus$, each of which is unsubstituted or monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{10}$aryl, $C_7$-$C_{16}$aralkyl, —$Si(R_3)_3$, —$Ge(R_3)_3$ or halogen, or both the $R_1$ radicals together are a divalent radical of the formula II

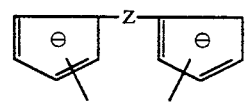

in which Z is —$(CH_2)_m$— where m=1,2 or 3, unsubstituted or phenyl-substituted $C_2$-$C_{12}$alkylidene, —$Si(R_3)_2$— or —$Si(R_3)_2$—O—$Si(R_3)_2$— and $R_3$ is $C_1$-$C_{12}$alkyl or $C_6$-$C_{10}$aryl, $R_2$ is a group of the formula IX

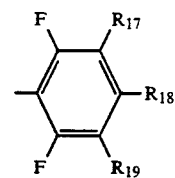

in which $R_{17}$ or $R_{18}$ is a group of the formula VI

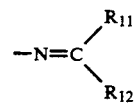

in which $R_{11}$ is $C_1$-$C_{12}$alkyl which is unsubstituted or substituted by halogen, $C_1$-$C_{12}$alkoxy or $C_2$-$C_8$dialkylamino, or $C_6$-$C_{14}$aryl, $C_7$-$C_{20}$aralkyl, $C_7$-$C_{20}$alkaryl, or $C_8$-$C_{20}$alkarylalkyl, each of which is unsubstituted or substituted by $C_1$-$C_8$alkoxy, —$(OCH_2CH_2)_p$—O—$C_1$-$C_{12}$alkyl where p=1-20, $C_1$-$C_8$alkylthio, $C_2$-$C_8$dialkylamino, halogen or nitro, and $R_{12}$ is hydrogen or has one of the meanings given for $R_{11}$, and the other radicals $R_{17}$, $R_{18}$ and $R_{19}$ are hydrogen or fluorine.

Of these compounds, those are preferred in which $R_1$ is cyclopentadienyl$^\ominus$ or $C_1$-$C_4$alkyl-substituted cyclopentadienyl⊖, in particular in which $R_1$ is cyclopentadienyl⊖.

Preferred compounds of the formula I are also those in which $R_2$ is a group of the formula IX in which $R_{17}$ is a group of the formula VI, and $R_{18}$ and $R_{19}$ are hydrogen. Of these, preferred compounds are those in which $R_{11}$ is phenyl or 2-furyl, each of which is unsubstituted or substituted by $C_1$-$C_{12}$alkyl, $C_1$-$C_4$alkoxy, $C_1$-$C_4$alkylthio, halogen or nitro, and $R_{12}$ is hydrogen.

These compounds can be used as photoinitiators for the photopolymerization of ethylenically unsaturated compounds. Details on the use of titanocenes as photoinitiators are given in EP-A-0,318,894. The novel compounds of the formula I can be used analogously. The titanocenes according to the invention are furthermore important intermediates in the preparation of titanocenes containing fluorinated aminoaryl ligands, which cannot be prepared by direct methods. The group of the formula VI can be converted into the $NH_2$ group by acid hydrolysis without hydrolytic cleavage of the titanium-carbon bond occurring. Secondary products of bis(cyclopentadienyl)bis(2,6-difluoro-3-aminophenyl)-titanium are described in large number in EP-A-0,318,894.

The invention furthermore relates to a process for the preparation of titanocenes of the formula X

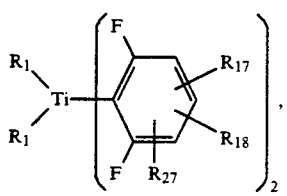

in which $R_1$ is cyclopentadienyl⊖, indenyl⊖ or 4,5,6,7-tetrahydroindenyl⊖, each of which is unsubstituted or monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{10}$aryl, $C_7$-$C_{16}$aralkyl, $-Si(R_3)_3$, $-Ge(R_3)_3$ or halogen, or the two $R_1$ radicals together are a divalent radical of the formula II

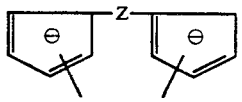

in which Z is $-(CH_2)_m-$ where $m=1,2$ or 3, unsubstituted or phenyl-substituted $C_2$-$C_{12}$alkylidene, $-Si(R_3)_2-$ or $-Si(R_3)_2-O-Si(R_3)_2-$, and $R_3$ is $C_1$-$C_{12}$alkyl or $C_6$-$C_{10}$aryl, $R_{17}$ and $R_{18}$, independently of one another, are hydrogen, fluorine or $C_1$-$C_4$alkyl, and $R_{27}$ is $-NH_2$ or a group of the formula XI or XIa

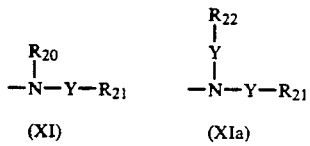

in which $R_{20}$ is hydrogen, linear or branched $C_1$-$C_{20}$alkyl, $C_2$-$C_{20}$alkenyl, $C_3$-$C_8$cycloalkyl, $C_4$-$C_{20}$cycloalkylalkyl or -alkylcycloalkyl, $C_5$-$C_{20}$alkylcycloalkyalkyl, $C_6$-$C_{20}$cycloalkenylalkyl, $C_6$-$C_{14}$aryl, $C_7$-$C_{20}$aralkyl or -alkaryl, $C_8$-$C_{20}$alkaralkyl or $C_3$-$C_{12}$trialkylsilyl, these radicals being unsubstituted or substituted by $C_1$-$C_{18}$alkoxy, $C_1$-$C_{18}$alkylthio, $C_1$-$C_{18}$alkylsulfonyl, $C_6$-$C_{10}$arylsulfonyl, $C_7$-$C_{20}$alkarylsulfonyl, 2-tetrahydrofuranyl or cyano, $R_{21}$ has one of the meanings given for $R_{20}$ or is $C_1$-$C_{20}$haloalkyl, $C_2$-$C_{20}$alkyl which is interrupted by $-CO-$ or $C_1$-$C_{12}$alkyl which is substituted by $-COOH$ or $-COOR_{23}$, in which $R_{23}$ is $C_1$-$C_{12}$alkyl, $C_5$-$C_{12}$cycloalkyl, $C_6$-$C_{16}$aryl or $C_7$-$C_{16}$aralkyl, and, in the case where Y is $-CO-$, $-CS-$ or $-SO_2-$, may alternatively be $-NR_{24}R_{25}$ in which $R_{24}$ and $R_{25}$, independently of one another, have one of the meanings given for $R_{20}$, or $R_{24}$ and $R_{25}$ together are $C_3$-$C_7$alkylene, which may be interrupted by $-O-$, $-S-$ or $-N(R_{26})-$ in which $R_{26}$ is hydrogen, $C_1$-$C_{12}$alkyl, $C_3$-$C_{12}$alkenyl, $C_7$-$C_{12}$aralkyl or $C_2$-$C_{20}$alkanoyl, or $R_{20}$ and $R_{21}$ together are linear or branched $C_2$-$C_8$alkylene, $C_2$-$C_8$alkylene which is substituted by halogen, $C_1$-$C_4$alkoxy, allyloxy or $-NR_{24}R_{25}$, or are a divalent radical of the formula

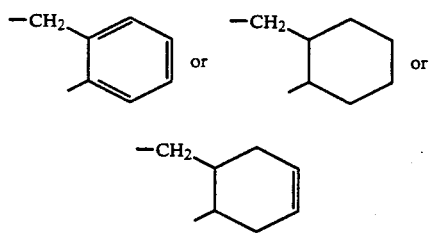

or $-Y-R_{21}$ is $R_{20}$ with the exception of hydrogen, Y is a $-CO-$, $-CS-$, $-COO-$, $-SO_2-$ or $-Si(R_{23})_2-$ group, in which $R_{23}$ is defined above, $R_{22}$ has one of the meanings given for $R_{21}$, or $R_{22}$ and $R_{21}$ together are $C_1$-$C_8$alkanediyl, $C_2$-$C_8$alkenediyl, $C_6$-$C_{14}$arenediyl, $C_4$-$C_{12}$cycloalkanediyl, $C_5$-$C_{12}$cycloalkenediyl, $C_6$-$C_{14}$cycloalkadienediyl, $C_7$-$C_{20}$bicycloalkanediyl, $C_7$-$C_{20}$bicycloalkenediyl or $C_2$-$C_4$alkanediyl which is interrupted by $-O-$, $-S-$ or $-N(R_{26})-$, these radicals being unsubstituted or substituted by one or more of the substituents halogen, $C_1$-$C_{10}$alkoxy, $C_1$-$C_{20}$alkyl, $C_3$-$C_{20}$alkenyl or $C_6$-$C_{14}$aryl, which comprises reacting 1 mole-equivalent of a compound of the formula $(R_1)_2TiX_2$ in which $R_1$ is as defined above and X is Cl, Br or I, and 2 mole-equivalents of an azomethine of the formula XII

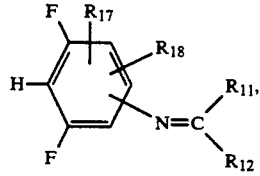

in which $R_{11}$ is $C_1$-$C_{12}$ alkyl which is unsubstituted or substituted by halogen, $C_1$-$C_{12}$alkoxy or $C_2$-$C_8$dialkylamino, or $C_6$-$C_{14}$aryl, $C_7$-$C_{20}$aralkyl, $C_7$-$C_{20}$alkaryl or $C_8$-$C_{20}$alkarylalkyl, each of which is unsubstituted or substituted by $C_1$-$C_8$alkoxy, $-(OCH_2CH_2)_p-O-C_1$-$C_{12}$alkyl where $p=1$-20, $C_1$-$C_8$alkylthio, $C_2$-$C_8$dialkylamino, halogen or nitro, and $R_{12}$ is hydrogen or has one of the meanings given for $R_{11}$, with 2 to 2.5 mole-equivalents of a lithium amide of the formula $LiN(R_{15})(R_{16})$ in which $R_{15}$ and $R_{16}$ are as defined in claim 1, at $-30°$ C. to 25° C. in an inert solvent to give a titanocene of the formula XIII

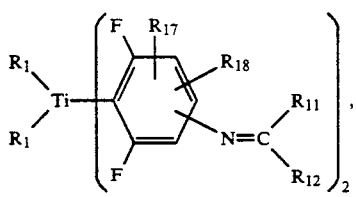

in which $R_{17}$, $R_{18}$, $R_{11}$ and $R_{12}$ are as defined above, hydrolysing the latter, and, if desired, converting the resultant $NH_2$ product of the formula

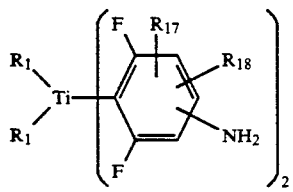

into the compound of the formula X by known alkylation and acylation methods.

The titanocenes of the formula X are useful photoinitiators. They are described in more detail in EP-A 0,318,839, as is their use. Compounds of the formula XIV can be converted into compounds of the formula X by customary alkylation and acylation methods, as outlined, for example, in EP-A 0,318,893 for the precursors of the formulae VI and VIIa (see, for example, page 9, line 11, to page 10, line 8. See also the subsequent Example 11).

Compounds of the formula XIV can be converted into compounds of the formula X by reaction, for example, with compounds of the formulae

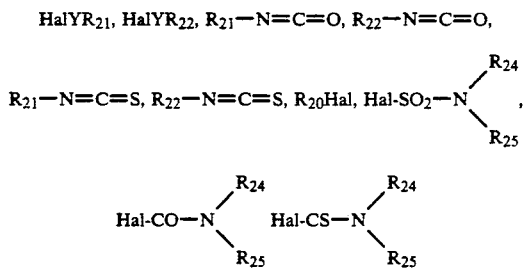

Hal-Y—$R_{21}$—$R_{22}$—Y-Hal, in which Hal is halogen (Cl, Br or I).

The examples below further illustrate the novel process and the products which can be prepared thereby. In these examples, all temperatures are given in °C. Percentages and parts in these examples and in the remainder of the description and in the patent claims relate to the weight, unless otherwise stated.

EXAMPLE 1

Preparation of bis(cyclopentadienyl)bis[2,6-difluoro-3(1-pyrryl)-phenyl]titanium Method A (Reaction at −10° C. Acid-aqueous work-up)

13.1 ml of a 1.6 molar solution of butyllithium in hexane (0.02 mol) are added dropwise at 0° C. to a stirred solution of 3 ml (0.02 mol) of distilled diisopropylamine in 20 ml of dry tetrahydrofuran (THF) under argon as protective gas. The resultant solution is added dropwise over the course of 30 minutes at −10° C. to a stirred suspension of 2.5 g (0.01 mol) of dicyclopentadienyltitanium dichloride and 3.96 g (0.022 mol) of N-(2,4-difluorophenyl)pyrrole in 20 ml of THF under argon as protective gas.

After the mixture has been stirred for a further 30 minutes, the cooling is removed. When the resultant suspension has reached room temperature, a solution of 2.5 g of oxalic acid in 10 ml of THF is added. Water is added, and the mixture is extracted with ethyl acetate. The organic phase is dried over $MgSO_4$ and evaporated in vacuo. The crude product is evaporated in ethyl acetate/petroleum ether 1:4 and purified by chromatography on a silica gel ($SiO_2$) column, to give 4.7 g (87.8% of theory) as orange crystals which melt at 160°–163°.

Method B (Reaction at −10° C. Acid-ethanolic work-up)

315 ml of a 1.52 molar solution of butyllithium in hexane (0.48 mol) are added dropwise at 0° C. to a solution of 68 ml (0.48 mol) of diisopropylamine in 145 ml of absolute tetrahydrofuran (THF) under $N_2$. This solution is added dropwise over the course of 1½ hours at −10° C. to a suspension of 56.9 g (0.228 mol) of dicyclopentadienyltitanium dichloride and 81.9 g (0.457 mol) of N-(2,4-difluorophenyl)pyrrole in 145 ml of THF. The cooling is subsequently removed, and the mixture is stirred until room temperature is reached. The reaction mixture is then concentrated by half in vacuo and poured into a mixture of 510 ml of 75% aqueous ethanol and 27.4 ml of acetic acid (0.48 mol). During this operation the product precipitates in crystalline form. The mixture is cooled to 0° C., and the product is filtered off and washed with 50% aqueous ethanol. Drying in vacuo at 40° C. gives 103 g (84.3% of theory) of orange crystals which melt at 156°–160° C.

Method C (Reaction at −10° C. Anhydrous work-up)

The procedure is as in methd A or B, but the work-up is as follows: the reaction mixture is evaporated to dryness in vacuo. The residue is taken up in methylene chloride, and the solution is freed from LiCl by filtration and re-evaporated. The crude product is dissolved in toluene and crystallization is induced by adding ethanol. The crude product of melting point 163°–165° C. is obtained in a yield of 65.6% of theory. A further 30% are obtained by chromatography of the mother liquor.

Method D (Reaction at room temperature. Acid-aqueous work-up)

The procedure is as in method A or B, but the dropwise addition of the lithium diisopropylamide solution is carried out at room temperature. Work-up involves adding aqueous acetic acid, evaporating the organic phase and crystallizing the product from ethanol. The product is obtained in 80% yield and melts at 160°–162° C.

EXAMPLE 2

Preparation of compounds of the formula

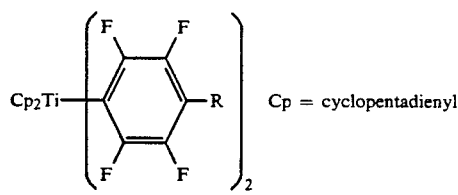   Cp = cyclopentadienyl

The following compounds of the above formula are prepared analogously to Example 1, method A.

EXAMPLE 3

Preparation of compounds of the formula

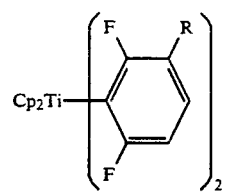

The following compounds of the above formula are prepared analogously to Example 1.

| R | Reaction temperature | Yield | Melting point | Method |
|---|---|---|---|---|
| H | 0° C. | 88.5% | 180–185° C. | A |
| —OC$_4$H$_9$ | −18° C. | 81.3% | 90–95° C. | A |
| —N(CH$_3$)$_2$ | −10° C. | 66.4% | 128–130° C. | A |
| —N⟨pyrroline⟩ | −3° C. | 87.8% | 160–165° C. | A |
| —N⟨2,5-dimethylpyrroline⟩ | −10° C. | 44.0% | 114–116° C. | A |
| —N⟨C(CH$_3$)$_2$-C(=O)⟩ (β-lactam) | −18° C. | 61.5% | 130–140° C. | A |
| —OSi(CH$_3$)$_3$ | −10° C. | 73.5% | <20° C. | C |
| —O-tetrahydropyranyl | −10° C. | 54.5% | 85–93° C. | A |
| —N(C$_4$H$_9$)—SO$_2$—C$_6$H$_4$—CH$_3$ | −10° C. | 48.9% | 76–80° C. | A |

| R | Reaction temperature | Yield | Melting point |
|---|---|---|---|
| H | −15° C. | 65.3% | 180–187° C. |
| F | +23° C. | 64.3% | 216–220° C. |
| —OC$_2$H$_5$ | −20° C. | 75.2% | 167–170° C. |
| —N(C$_4$H$_9$)$_2$ | −18° C. | 65.5% | 92–98° C. |
| —OC$_{10}$H$_{21}$ | −10° C. | 47.1% | liquid* |

*Elemental analysis: Calculated: 63.96% C, 6.65% H   Found: 63.29% C, 6.76% H

EXAMPLE 4

Preparation of compounds of the formula

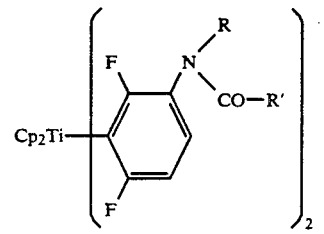

The following compounds of the above formula are prepared analogously to Example 1, method A.

| R | | Reaction temperature | Yield | Melting point |
|---|---|---|---|---|
| n-Hexyl | $-\text{C}(\text{CH}_3)(\text{CH}_3)-\text{C}_2\text{H}_5$ | $-18°$ C. | 84.6% | 98–103° C. |
| 2-Ethylhexyl | Phenyl | $-10°$ C. | 71.8% | 80–86° C. |
| Cyclohexylmethyl | p-Tolyl | $-10°$ C. | 68.6% | 130–140° C. |
| n-Hexyl | Phenyl | $-10°$ C. | 69.2% | 78–88° C. |
| n-Butyl | Phenyl | $-10°$ C. | 70% | 180–185° C. |
| t-Butyl | $-\text{C}(\text{CH}_3)(\text{CH}_3)-\text{CH}_2\text{CH}_2\text{Cl}$ | $-10°$ C. | 70.5% | 95–100° C. |
| 2-Ethylhexyl | Phenyl | $-30°$ C. | 71.7% | 80–86° C. |
| Cyclohexylmethyl | $-\text{C}(\text{CH}_3)(\text{C}_2\text{H}_5)-(\text{CH}_2)_4-\text{CH}_3$ | $-10°$ C. | 71.2% | 85–90° C. |
| Cyclohexylmethyl | 4-Chlorophenyl | $-10°$ C. | 69.9% | 133–135° C. |
| n-Hexyl | $-\text{C}(\text{CH}_3)(\text{C}_2\text{H}_5)-(\text{CH}_2)_4-\text{CH}_3$ | $-10°$ C. | 74.7% | 45–55° C. |

EXAMPLE 5

Preparation of compounds of the formula

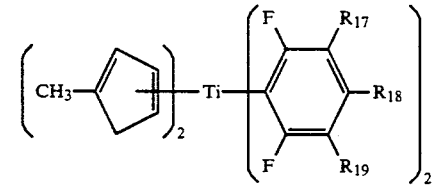

The following compounds of the above formula are prepared analogously to Example 1, method A.

| $R_{17}$ | $R_{18}$ | $R_{19}$ | Reaction temperature | Yield | Melting point |
|---|---|---|---|---|---|
| H | H | H | $-10°$ C. | 54.1% | 152–158° C. |
| H | F | H | $+10°$ C. | 63.6% | 155–165° C. |
| F | F | F | $-20°$ C. | 52.2% | 185–193° C. |
| F | $-\text{OC}_2\text{H}_5$ | F | $+10°$ C. | 52% | 155–160° C. |
| F | $-\text{N}(\text{C}_4\text{H}_9)_2$ | F | $-20°$ C. | 80.2% | Oil |
| $-\text{OC}_4\text{H}_9$ | H | H | $0°$ C. | 88.2% | 85–90° C. |
| $-\text{N}\diagup\diagdown$ (pyrrolyl) | H | H | $0°$ C. | 76.4% | 73–83° C. |
| $-\text{N}(\text{C}_6\text{H}_{13})\text{CO}-\text{C}(\text{CH}_3)(\text{CH}_3)-\text{C}_2\text{H}_5$ | H | H | $-20°$ C. | 75.2% | 50–60° C. |

EXAMPLE 6

Preparation of compounds of the formula

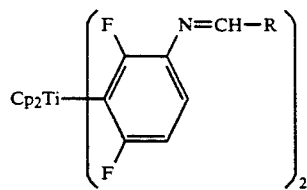

The compounds of the above formula are prepared analogously to Example 1, method C.

| R | Reaction temperature | Melting point | | Analysis (%) | | |
|---|---|---|---|---|---|---|
| | | | | C | H | N |
| Phenyl | $-20°$ C. | 135–145° C. | calc. | 70.8 | 4.3 | 4.6 |
| | | | found | 70.8 | 4.7 | 4.2 |
| 4-Methoxyphenyl | $-20°$ C. | 117° C. (decomp.) | calc found | 68.1 68.6 | 4.5 4.2 | 4.2 3.6 |
| 4-Chlorophenyl | $-20°$ C. | 210–213° C. | calc. found | 63.6 63.4 | 3.6 3.6 | 4.1 4.0 |
| 4-Methylphenyl | $-20°$ C. | 210–213° C. | calc. found | 71.5 71.0 | 4.7 4.9 | 4.4 4.3 |
| 3-Nitrophenyl | $-20°$ C. | 120° C. (decomp.) | calc. found | 61.7 61.7 | 3.5 3.5 | 8.0 7.8 |

EXAMPLE 7

Preparation of the azomethine derivatives

N-Benzal-2,4-difluoroaniline 322.8 g (2.5 mol) of 2,4-difluoroaniline, 265.3 g (2.5 mol) of benzaldehyde and 1000 ml of toluene are heated to reflux, and the water formed is removed for 5 hours at 90°–105° C. using a water separator. The toluene is removed by distillation on a vacuum rotary evaporator, and the product is recrystallized from hexane, to give 516.9 g (92.5 % of theory) of N-benzal-2,4-difluoroaniline, which melts at 51°–52° C.

N-(4-Methylbenzal)-2,4-difluoroaniline

N-(4-Methylbenzal)-2,4-difluoroaniline is obtained analogously from p-toluylaldehyde in a yield of 81% of theory. The white crystals from hexane melt at 67° C.

| Elemental analysis: $C_{14}H_{11}F_2N$ | | | |
|---|---|---|---|
| | C | H | N |
| Calculated: | 72.72% | 4.79% | 6.06% |
| Found: | 72.72% | 4.83% | 5.88% |

EXAMPLE 8

Hydrogenation of the azomethine derivatives

N-Benzyl-2,4-difluoroaniline 195.4 g (0.9 mol) of N-benzal-2,4-difluoroaniline are dissolved in 900 ml of tetrahydrofuran in an autoclave. 19 g of Raney nickel and 2 g of acetic acid are added, and the mixture is hydrogenated at 60° to 85° C. and a hydrogen pressure of 100 bar. The end point of the reaction is determined by thin-layer chromatography or gas chromatography. The suspension is filtered and the solution is evaporated on a vacuum rotary evaporator. The residue is distilled in vacuo at 102° C. and 3.6 mbar, to give 125.6 g (64% of theory) of a pale yellow liquid.

| Elemental analysis: $C_{13}H_{11}F_2N$ | | | |
|---|---|---|---|
| | C | H | N |
| Calculated: | 71.22% | 5.06% | 6.39% |
| Found: | 71.07% | 5.16% | 6.38% |

N-(2,4-Difluorophenyl)-4-methylbenzylamine is prepared analogously. The residue is recrystallized from hexane, to give 121.1 g (65% of theory) of white crystals which melt at 42°–44° C.

| Elemental analysis: $C_{14}H_{13}F_2N$ | | | |
|---|---|---|---|
| | C | H | N |
| Calculated: | 72.09% | 5.62% | 6.00% |
| Found: | 71.44% | 5.63% | 6.20% |

EXAMPLE 9

Preparation of the 2,4-difluoroanilides

N-Benzyl-N-(2,2-dimethylpentanoyl)-2,4-difluoroaniline 17.5 g (80 mmol) of N-benzyl-2,4-difluoroaniline and 16.2 g (160 mmol) of triethylamine are dissolved in 100 ml of ether in a round-bottomed flask. 11.9 g (80 mmol) of 2,2-dimethylpentanoyl chloride in 30 ml of ether are slowly added to this solution at room temperature. The mixture is subsequently stirred overnight. Triethylammonium chloride slowly precipitates out. When the reaction is complete, the suspension is diluted with 250 ml of ether and poured into 250 ml of water. The mixture is acidified using 5% hydrochloric acid solution. The two phases are separated, and the organic phase is washed twice with water, dried using $MgSO_4$ and evaporated on a vacuum rotary evaporator. The residue, a colourless oil, solidifies on standing and melts at 55°–60° C.

| Elemental analysis: $C_{20}H_{23}F_2NO$ | | | |
|---|---|---|---|
| | C | H | N |
| Calculated: | 72.49% | 7.00% | 4.23% |
| Found: | 72.39% | 6.95% | 4.22% |

N-(4-Methylbenzyl)-N-(2,2-dimethylpentanoyl)-2,4-difluoroaniline is prepared analogously from N-(2,4-difluorophenyl)-4-methylbenzylamine. The white crystals melt at 76°–77° C.

| Elemental analysis: $C_{21}H_{25}F_2NO$ | | | |
|---|---|---|---|
| | C | H | N |
| Calculated: | 73.02% | 7.29% | 4.05% |
| Found: | 73.07% | 7.53% | 4.01% |

EXAMPLE 10

Preparation of the titanocenes a) Bis(cyclopentadienyl)bis[2,6-difluoro-3-(N-benzyl-2,2-dimethylpentanoylamino)phenyl]thitanium Starting from N-benzyl-N-(2,2-dimethylpentanoyl)-2,4-difluoroaniline, the corresponding titanocene is prepared at −10° C. analogously to Example 1, method A. Chromatographic purification over a silica gel column gives a glassy orange product.

| Elemental analysis: $C_{50}H_{54}F_4N_2O_2Ti$ | | | |
|---|---|---|---|
| | C | H | N |
| Calculated: | 71.59% | 6.49% | 3.34% |
| Found: | 71.40% | 6.62% | 2.87% | b) Bis(cyclopentadienyl)bis[2,6-difluoro-3-(N-(4-methylbenzyl)-2,2-dimethylpentanoylamino) phenyl]titanium is prepared analogously from N-(4-methylbenzyl)-N-(2,2-dimethylpentanoyl)-2,4-difluoroaniline. Purification gives a glassy orange product.

| Elemental analysis: $C_{52}H_{58}F_4N_2O_2Ti$ | | | |
|---|---|---|---|
| | C | H | N |
| Calculated: | 72.04% | 6.74% | 3.23% |
| Found: | 71.08% | 7.02% | 2.79% |

EXAMPLE 11

Preparation of bis(cyclopentadieny)bis(2,6-difluoro-3-aminophenyl)-titanium without isolation of the azomethine intermediate bis(cyclopentadienyl)bis[2,6-difluoro-3-(N-benzalamino)phenyl]titanium 477.9 g (2.2 mol) of N-benzal-2,4-difluoroaniline are reacted at −10° C. with 248.8 g (1.0 mol) of titanocene dichloride analogously to Example 1, method A, to give bis(cyclopentadienyl)bis[2,6-difluoro-3-(N -benzalamino)phenyl]titanium. When the yellow-brown suspension produced has reached room temperature, it is evaporated on a vacuum rotary evaporator. The residue is taken up in 3000 ml of methylene chloride and clarified over Hyflo. The filtrate is re-evaporated. The residue is dissolved in 2000 ml of ethyl acetate, and 2000 ml of 2N hydrochloric acid solution are added. After hydrolysis has been carried out by stirring the mixture for 3 hours, the phases are separated. The organic phase is extracted three times with 200 ml of 2N hydrochloric acid solution in each case. The aqueous phases are combined and washed once with 500 ml of ethyl acetate. 500 ml of ethanol are added to the water phase, and the mixture is then neutralized using 30% sodium hydroxide solution with cooling at 10°–15° C. The mixture is then cooled to 5° C. The red-brown suspension produced is filtered and dried at 40° C. in vacuo, to give 391.8 g (90.2% of theory) of orange-red crystals which melt at 250° C. with decomposition.

| Elemental analysis: $C_{22}H_{18}F_4N_2Ti$ | | | |
|---|---|---|---|
| | C | H | N |
| Calculated: | 60.84% | 4.18% | 6.45% |
| Found: | 60.93% | 4.37% | 6.19% |

EXAMPLE 12

Photocuring of an acrylate mixture

A photocurable composition is prepared by mixing the following components:

| | | Solids content |
|---|---|---|
| 150.30 g | of Scriptset 540[1)] (30% solution in acetone) | 45.1 g |
| 48.30 g | of trimethylolpropane triacrylate | 48.3 g |
| 6.60 g | of polyethylene glycol diacrylate | 6.6 g |
| 0.08 g | of crystal violet | |
| 205.28 g | | 100.0 g |

[1)]Polystyrene-maleic anhydride copolymer (Monsanto)

Portions of this composition are in each case mixed with 0.3% (relative to the solids content) of photoinitiator. All operations are carried out under a red light.

The samples mixed with initiator are applied in a thickness of 150 μm to 200 μm aluminium foil (10×15 cm). The solvent is removed by warming at 60° C. for 15 minutes in a circulating oven. A 76 μm thick polyester film is placed on the liquid coating, and this is covered by a standardized test negative with 21 steps of different optical density (Stouffer wedge). This is covered by a second polyester film, and the resultant laminate is fixed onto a metal plate. The sample is exposed with a 5 kW metal halide lamp at a distance of 30 cm for 10 seconds for a first test series, for 20 seconds for a second test series and for 40 seconds for a third test series. After the exposure, the films and the mask are removed, the exposed coating is developed in an ultrasound bath for 120 seconds using developer A and subsequently dried at 60° C. for 15 minutes in a circulating oven. Sensitivity of the initiator system used is characterized by indicating the final wedge step imaged without adhesion. The higher the number of steps, the more sensitive the system. An increase by two steps indicates an approximate doubling of the curing rate. The results are given in Table 1. Developer A contains 15 g of sodium metasilicate.9 H$_2$O; 0.16 g of KOH; 3 g of polyethylene glycol 6000; 0.5 g of levulinic acid and 1000 g of deionized water.

TABLE 1

| Titanocene Example | Number of imaged steps after exposure for | | |
|---|---|---|---|
| | 10s | 20s | 40s |
| 10a | 9 | 12 | 14 |
| 10b | 8 | 10 | 12 |

EXAMPLE 13

Photocuring of a monomer/polymer mixture

A photocurable composition is prepared by mixing the following components:

| 37.64 g | of Sartomer SR 444 (pentaerythritol triacrylate) (Sartomer Company, Westchester) |
|---|---|
| 10.76 g | of Cymel 301 (hexamethoxymethylmelamine) (Cyanamid) |
| 47.30 g | of Carboset 525 (thermoplastic polyacrylate containing carboxyl groups/B. F. Goodrich) |
| 4.30 g | of polyvinylpyrrolidone PVP (GAF) |
| 100.00 g | of the above mixture |
| 0.50 g | of Irgalit Green GLN |
| 319.00 g | of methylene chloride |
| 30.00 g | of methanol |
| 450.00 g | |

Portions of this composition are in each case mixed with 0.3% (relative to the solids content) of the titanocenes given in the table below. All operations are carried out under a red light.

The samples mixed with initiator are applied in a thickness of 200 μm to 200 μm aluminium foil (10×15 cm). The solvent is removed by warming at 60° C. for 15 minutes in a circulating oven. A 76 μm thick polyester film is placed on the liquid coating, and this is covered by a standardized test negative with 21 steps of different optical density (Stouffer wedge). This is covered by a second polyester film, and the resultant laminate is fixed onto a metal plate. The sample is exposed with a 5 kW metal halide lamp at a distance of 30 cm for 10 seconds for a first test series, for 20 seconds for a second test series and for 40 seconds for a third test series. After the exposure, the films and the mask are removed, the exposed coating is developed in an ultrasound bath for 240 seconds using developer A and subsequently dried at 60° C. for 15 minutes in a circulation oven. Sensitivity of the initiator system used is characterized by indicating the final wedge step imaged without adhesion. The higher the number of steps, the more sensitive the system. An increase by two steps indicates an approximate doubling of the curing rate. The results are given in Table 2.

| Titanocene Example | Number of imaged steps after exposure for | | |
|---|---|---|---|
| | 10s | 20s | 40s |
| 10a | 9 | 12 | 15 |
| 10b | 7 | 10 | 13 |

What is claimed is:

1. A process for the preparation of a titanocene of the formula I

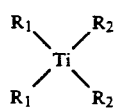

in which R$_1$ is cyclopentadienyl$^\ominus$, indenyl$^\ominus$ or 4,5,6,7-tetrahydroindenyl$^\ominus$, each of which is unsubstituted or monosubstituted or polysubstituted by C$_1$–C$_{18}$alkyl, C$_1$–C$_{18}$alkoxy, C$_2$–C$_{18}$alkenyl, C$_5$–C$_8$cycloalkyl, C$_6$–C$_{10}$aryl, C$_7$–C$_{16}$aralkyl, —Si(R$_3$)$_3$, —Ge(R$_3$)$_3$ or halogen, or both R$_1$ radicals together are a divalent radical of the formula II

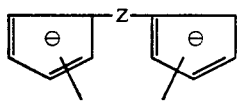

in which Z is —(CH$_2$)$_m$— where m=1,2 or 3, unsubstituted or phenyl-substituted C$_2$-C$_{12}$alkylidene, —Si(R$_3$)$_2$— or —Si(R$_3$)$_2$—O—Si(R$_3$)$_2$—, and R$_3$ is C$_1$-C$_{12}$alkyl or C$_6$-C$_{10}$aryl, R$_2$ is a six-membered carbocylic aromatic ring which is substituted by fluorine in both the ortho positions to the Ti-C bond and which, in addition, may be substituted by further fluorine atoms, by C$_1$-C$_4$alkyl or by one of the groups III to VII,

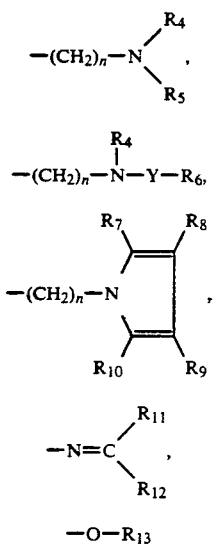

in which n is an integer from 0 to 6, R$_4$ is C$_1$-C$_{20}$alkyl, C$_3$-C$_{10}$cycloalkyl, C$_4$-C$_{20}$cycloalkylalkyl, C$_4$-C$_{20}$alkylcycloalkyl, C$_5$-C$_{20}$alkylcycloalkylalkyl, C$_6$-C$_{14}$aryl, C$_7$-C$_{20}$aralkyl, C$_7$-C$_{20}$alkaryl, C$_8$-C$_{20}$alkaralkyl, C$_3$-C$_{12}$alkoxyalkyl, tetrahydrofurfuryl or a —(CH$_2$CH$_2$O)$_p$—C$_1$-C$_{12}$alkyl radical where p=1-20, R$_5$ has one of the meanings given for R$_4$, or R$_4$ and R$_5$ together are C$_3$-C$_8$alkylene, which may be interrupted by —O—, —S— or —N(R$_{14}$)—, or R$_4$ and R$_5$ together are —Si(R$_3$)$_2$—CH$_2$CH$_2$—Si(R$_3$)$_2$—, Y is —CO—, —CS—, —COO—, —CON(R$_{14}$)—, —SO$_2$—, —SO$_2$N(R$_{14}$)— or —Si(R$_3$)$_2$—, R$_6$ is C$_4$-C$_{20}$alkyl, C$_2$-C$_{20}$alkaryl, C$_4$-C$_{10}$cycloalkyl, C$_5$-C$_{20}$cycloalkylalkyl, C$_5$-C$_{20}$alkylcycloalkyl, C$_6$-C$_{20}$alkylcycloalkylalkyl, C$_6$-C$_{14}$aryl, C$_7$-C$_{20}$aralkyl, C$_7$-C$_{20}$alkaryl or C$_8$-C$_{20}$alkarylalkyl, it being possible for these radicals to be unsubstituted or substituted by C$_1$-C$_{18}$alkoxy, C$_1$-C$_{18}$alkylthio or halogen, or R$_6$ and R$_4$ together are C$_4$-C$_8$alkylene, which may be interrupted by —O—, —S— or —N(R$_{14}$)—, with the proviso that the C atom of R$_6$ which is adjacent to Y does not carry an H atom if Y is —CO—, —CS— or —SO$_2$—, R$_7$, R$_8$, R$_9$ and R$_{10}$, independently of one another, are hydrogen, C$_1$-C$_{18}$alkyl, C$_2$-C$_5$alkenyl, C$_7$-C$_9$phenylalkyl or C$_7$-C$_{12}$alkylphenyl, each of which is unsubstituted or substituted by C$_2$-C$_8$dialkylamino, bis[2-(C$_1$-C$_4$alkoxy)ethyl]amino, morpholino, piperidino, C$_2$-C$_{12}$alkoxy, —(OCH$_2$CH$_2$)$_p$—O—C$_1$-C$_{12}$alkyl where p=1-20, 1,3-dioxolan-2-yl, C$_1$-C$_{12}$alkylthio or halogen, or are 2-furyl or —Si(R$_3$)$_3$, R$_{11}$ is C$_1$-C$_{12}$alkyl which is unsubstituted or substituted by halogen, C$_1$-C$_{12}$alkoxy or C$_2$-C$_8$dialkylamino, or C$_6$-C$_{14}$aryl, C$_7$-C$_{20}$aralkyl, C$_7$-C$_{20}$alkaryl or C$_8$-C$_{20}$alkarylalkyl, each of which is unsubstituted or substituted by C$_1$-C$_8$alkoxy, —(OCH$_2$CH$_2$)$_p$—O—C$_1$-C$_{12}$alkyl where p=1-20, C$_1$-C$_8$alkylthio, C$_2$-C$_8$dialkylamino, halogen or nitro, R$_{12}$ is hydrogen or has one of the meanings given for R$_{11}$, R$_{13}$ is C$_1$-C$_{18}$alkyl, C$_3$-C$_{12}$cycloalkyl, C$_2$-C$_5$alkenyl, glycidyl, —(CH$_2$CH$_2$O)$_p$—C$_1$-C$_{12}$alkyl where p=1-20, C$_6$-C$_{10}$aryl, C$_7$-C$_{20}$aralkyl, C$_7$-C$_{20}$alkaryl or C$_8$-C$_{20}$alkarylalkyl, it being possible for the aryl radicals to be substituted by C$_1$-C$_4$alkoxy, C$_1$-C$_4$alkylthio, C$_2$-C$_8$dialkylamino, halogen or nitro, or R$_{13}$ is C$_1$-C$_{20}$haloalkyl, —Si(R$_3$)$_3$, —Sn(R$_3$)$_3$ or 2-tetrahydropyranyl, and R$_{14}$ is C$_1$-C$_{12}$alkyl, C$_3$-C$_5$alkaryl or C$_7$-C$_9$phenylalkyl, by reacting a compound of the formula VIII

in which X is Cl, Br or I, with LiR$_2$, which comprises reacting a mixture of 1 mole-equivalent of the compound of the formula VIII and 2 mole-equivalents of a compound HR$_2$ with 2 to 2.5 mole-equivalents of a lithium amide at −30° C. to 25° C. in an inert solvent, the lithium amide being a compound of the formula LiN(R$_{15}$)(R$_{16}$), in which R$_{15}$ and R$_{16}$, independently of one another, are 1-branched alkyl, cyclohexyl or phenyl, or R$_{15}$ and R$_{16}$, together with the N atom, are a 2,5-dialkylated pyrrolidine or a 2,6-dialkylated or 2,2,6,6-tetraalkylated piperidine.

2. A process according to claim 1, wherein 2.0 to 2.2 mole-equivalents of the lithium amide are used per mole-equivalent of the compound of the formula VIII.

3. A process according to claim 1, wherein the reaction is carried out at −20° C. to +25° C.

4. A process according to claim 1, wherein the reaction is carried out in the presence of a polar solvent.

5. A process according to claim 1, wherein the reaction is carried out in a mixture of polar and non-polar solvents.

6. A process according to claim 1, wherein a compound of the formula VIII is used in which X is chlorine.

7. A process according to claim 1, wherein the lithium amide used is lithium diisopropylamide, lithium cyclohexylisopropylamide, lithium dicyclohexylamide or lithium 2,2,6,6-tetramethylpiperidide.

8. A process according to claim 7, wherein the lithium amide used is lithium diisopropylamide.

9. A process according to claim 1, wherein R$_1$ is cyclopentadienyl$^\ominus$ or C$_1$-C$_4$alkyl-substituted cyclopentadienyl$^\ominus$.

10. A process according to claim 9, wherein R$_1$ is cyclopentadienyl$^\ominus$ or methylcyclopentadienyl$^\ominus$.

11. A process according to claim 1, wherein R$_2$ is a monovalent radical of the formula IX

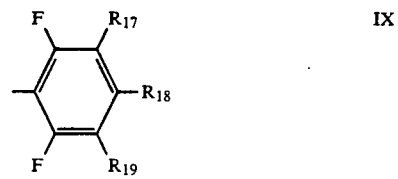

in which $R_{17}$, $R_{18}$ and $R_{19}$, independently of one another, are hydrogen, fluorine, $C_1$-$C_4$alkyl or a group of the formula III-VII.

12. A process according to claim 11, wherein, in the formula IX, $R_{17}$, $R_{18}$ and $R_{19}$, independently of one another, are hydrogen, fluorine or methyl.

13. A process according to claim 11, wherein, in the formula IX, $R_{17}$ or $R_{18}$ is a group of the formula III–VII, and the other radicals $R_{17}$, $R_{18}$ and $R_{19}$ are hydrogen or fluorine.

14. A process according to claim 13, wherein $R_{17}$ or $R_{18}$ is a group of the formula III-VII in which n is 0 or 1, $R_4$ is $C_1$-$C_{12}$alkyl, $C_3$-$C_{12}$alkoxy, phenyl, $C_7$-$C_9$phenylalkyl, cycloalkyl, cyclohexylmethyl or a —($CH_2C$-$H_2O)_p$—$C_1$-$C_4$alkyl group where p=1-5, $R_5$ has one of the meanings given for $R_4$, or $R_4$ and $R_5$ together are $C_4$-$C_5$alkylene, which may be interrupted by —O— or —N($R_{14}$)— where $R_{14}$ is $C_1$-$C_4$alkyl, Y is —CO—, —$SO_2$— or —COO—, $R_6$ is $C_4$-$C_{12}$alkyl, phenyl, or $CH_3$—, $CH_3O$— or Cl-substituted phenyl or $C_1$-$C_8$-haloalkyl or $R_6$ and $R_4$ together are $C_4$-$C_8$alkylene, with the proviso that the C atom of $R_6$ which is adjacent to Y does not carry an H atom, $R_7$, $R_8$, $R_9$ and $R_{10}$, independently of one another, are hydrogen, $C_1$-$C_8$alkyl, $C_2$-$C_{12}$alkoxyalkyl, $C_2$-$C_4$alkenyl, phenyl or 2-furyl, $R_{11}$ is phenyl which is unsubstituted or substituted by $C_1$-$C_{12}$alkyl, $C_1$-$C_4$alkoxy, $C_1$-$C_4$alkylthio, halogen or nitro, $R_{12}$ is hydrogen, and $R_{13}$ is $C_1$-$C_{14}$alkyl, —($CH_2CH_2O)_p$—$C_1$-$C_{12}$alkyl where p=1-20, phenyl, benzyl, 2-tetrahydropyranyl or —Si($CH_3)_3$.

15. A process according to claim 13, wherein, in the formula IX, $R_{17}$ is a group of the formula III-VII, and $R_{18}$ and $R_{19}$ are hydrogen.

16. A process according to claim 13, wherein, in the formula IX, $R_{18}$ is a group of the formula III-VII, and $R_{17}$ and $R_{19}$ are fluorine.

17. A process for the preparation of a titanocene of the formula X

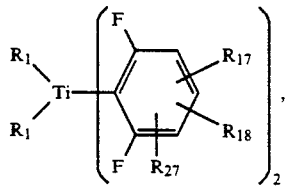
(X)

in which $R_1$ is cyclopentadienyl$^\ominus$, indenyl$^\ominus$ or 4,5,6,7-tetrahydroindenyl$^\ominus$, each of which is unsubstituted or monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{10}$aryl, $C_7$-$C_{16}$aralkyl, —Si($R_3)_3$, —Ge($R_3)_3$ or halogen, or the two $R_1$ radicals together are a divalent radical of the formula II

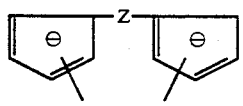
II in which Z is —($CH_2)_m$— where m=1,2 or 3, unsubstituted or phenyl-substituted $C_2$-$C_{12}$alkylidene, —Si($R_3$-$)_2$— or —Si($R_3)_2$—O—Si($R_3)_2$—, and $R_3$ is $C_1$-$C_{12}$alkyl or $C_6$-$C_{10}$aryl, $R_{17}$ and $R_{18}$, independently of one another, are hydrogen, fluorine or $C_1$-$C_4$alkyl, and $R_{27}$ is —$NH_2$ or a group of the formula XI or XIa

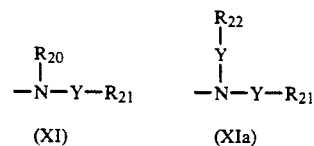

in which $R_{20}$ is hydrogen, linear or branched $C_1$-$C_{20}$alkyl, $C_2$-$C_{20}$alkenyl, $C_3$-$C_8$cycloalkyl, $C_4$-$C_{20}$cycloalkylalkyl or -alkylcycloalkyl, $C_5$-$C_{20}$alkylcycloalkylalkyl, $C_6$-$C_{20}$cycloalkenylalkyl, $C_6$-$C_{14}$aryl, $C_7$-$C_{20}$aralkyl or -alkaryl, $C_8$-$C_{20}$alkaralkyl or $C_3$-$C_{12}$-trialkylsilyl, these radicals being unsubstituted or substituted by $C_1$-$C_{18}$alkoxy, $C_1$-$C_{18}$alkylthio, $C_1$-$C_{18}$alkylsulfonyl, $C_6$-$C_{10}$arylsulfonyl, $C_7$-$C_{20}$alkarylsulfonyl, 2-tetrahydrofuranyl or cyano, $R_{21}$ has one of the meanings given for $R_{20}$ or is $C_1$-$C_{20}$haloalkyl, $C_2$-$C_{20}$alkyl which is interrupted by —CO— or $C_1$-$C_{12}$alkyl which is substituted by —COOH or —COOR$_{23}$, in which $R_{23}$ is $C_1$-$C_{12}$alkyl, $C_5$-$C_{12}$cycloalkyl, $C_6$-$C_{16}$aryl or $C_7$-$C_{16}$aralkyl, and, in the case where Y is —CO—, —CS— or —$SO_2$—, may alternatively be —$NR_{24}R_{25}$ in which $R_{24}$ and $R_{25}$, independently of one another, have one of the meanings given for $R_{20}$, or $R_{24}$ and $R_{25}$ together are $C_3$-$C_7$alkylene, which may be interrupted by —O—, —S— or —N($R_{26}$)— in which $R_{26}$ is hydrogen, $C_1$-$C_{12}$alkyl, $C_3$-$C_{12}$alkenyl, $C_7$-$C_{12}$aralkyl or $C_2$-$C_{20}$alkanoyl, or $R_{20}$ and $R_{21}$ together are linear or branched $C_2$-$C_8$alkylene, $C_2$-$C_8$alkylene which is substituted by halogen, $C_1$-$C_4$alkoxy, allyloxy or —$NR_{24}R_{25}$, or are a divalent radical fo the formula

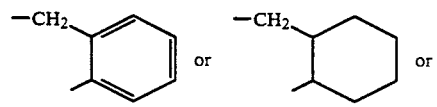

or —Y—$R_{21}$ is $R_{20}$ with the exception of hydrogen, Y is a —CO—, —CS—, —COO—, —$SO_2$— or —Si($R_{23})_2$— group, in which $R_{23}$ is as defined above, $R_{22}$ has one of the meanings given for $R_{21}$, or $R_{22}$ and $R_{21}$ together are $C_1$-$C_8$alkenediyl, $C_2$-$C_8$alkenediyl, $C_6$-$C_{14}$arenediyl, $C_4$-$C_{12}$cycloalkanediyl, $C_5$-$C_{12}$cycloalkenediyl, $C_6$-$C_{14}$cycloalkadienediyl, $C_7$-$C_{20}$bicycloalkanediyl, $C_7$-$C_{20}$bicycloalkenediyl or $C_2$-$C_4$alkanediyl which is interrupted by —O—, —S— or —N($R_{26}$)—, these radicals being unsubstituted or substituted by one or more of the substituents halogen, $C_1$-$C_{10}$alkoxy, $C_1$-$C_{20}$alkyl, $C_3$-$C_{20}$alkenyl or $C_6$-$C_{14}$aryl, which comprises reacting 1 mole-equivalent of a compound of the formula ($R_1)_2$Ti$X_2$ in which $R_1$ is as defined above and X is Cl, Br or I, and 2 mole-equivalents of an azomethine of the formula XII

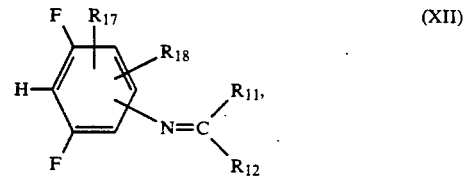
(XII)

in which $R_{11}$ is $C_1$–$C_{12}$alkyl which is unsubstituted or substituted by halogen, $C_1$–$C_{12}$alkoxy or $C_2$–$C_8$dialkylamino, or $C_6$–$C_{14}$aryl, $C_7$–$C_{20}$aralkyl, $C_7$–$C_{20}$alkaryl, or $C_8$–$C_{20}$alkarylalkyl, each of which is unsubstituted or substituted by $C_1$–$C_8$alkoxy, —(OCH$_2$CH$_2$)$_p$—O—C$_1$–$C_{12}$alkyl where p=1-20, $C_1$–$C_8$alkythio, $C_2$–$C_8$dialkylamino, halogen or nitro, and $R_{12}$ is hydrogen or has one of the meanings given for $R_{11}$, with 2 to 2.5 mole-equivalents of a lithium amide of the formula LiN($R_{15}$)($R_{16}$) in which $R_{15}$ and $R_{16}$ are as defined in claim 1, at $-30°$ C. to $25°$ C. in an inert solvent to give a titanocene of the formula XIII

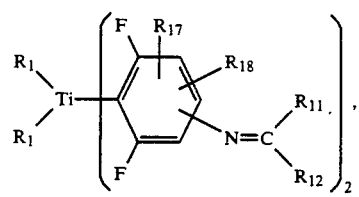
(XIII)

in which $R_{17}$, $R_{18}$, $R_{11}$ and $R_{12}$ are as defined above, hydrolysing the latter, and, if desired, converting the resultant NH$_2$ product of the formula

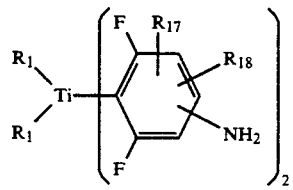
(XIV)

into the compound of the formula X by known alkylation and acylation methods.

* * * * *